(12) United States Patent
Katz et al.

(10) Patent No.: US 8,777,923 B2
(45) Date of Patent: *Jul. 15, 2014

(54) PATIENT MONITORING AND DRUG DELIVERY SYSTEM AND METHOD OF USE

(75) Inventors: Hal H. Katz, Jupiter, FL (US); Matthew T. Nesbitt, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 18 days.

This patent is subject to a terminal disclaimer.

(21) Appl. No.: 12/911,788

(22) Filed: Oct. 26, 2010

(65) Prior Publication Data

US 2011/0040158 A1 Feb. 17, 2011

Related U.S. Application Data

(63) Continuation of application No. 10/791,959, filed on Mar. 3, 2004, now Pat. No. 7,833,213.

(60) Provisional application No. 60/451,860, filed on Mar. 4, 2003.

(51) Int. Cl.
*A61M 31/00* (2006.01)

(52) U.S. Cl.
USPC ............................................ 604/500; 604/67

(58) Field of Classification Search
USPC ............... 604/511, 920, 97.02, 595, 131, 19, 604/930.1, 573, 500, 26, 144, 65–67, 604/93.01; 128/898; 600/595, 573, 26
See application file for complete search history.

(56) References Cited

U.S. PATENT DOCUMENTS

| | | | |
|---|---|---|---|
| 4,078,562 A | 3/1978 | Friedman |
| 4,308,866 A | 1/1982 | Jelliffe et al. |
| 4,392,849 A | 7/1983 | Petre et al. |
| 4,688,577 A | 8/1987 | Bro |
| 4,756,706 A | 7/1988 | Kerns et al. |
| 4,895,161 A | 1/1990 | Cudahy et al. |
| 5,417,222 A | 5/1995 | Dempsey et al. |
| 5,447,164 A | 9/1995 | Shaya et al. |
| 5,482,438 A | 1/1996 | Anderson et al. |
| 5,522,798 A | 6/1996 | Johnson et al. |

(Continued)

FOREIGN PATENT DOCUMENTS

| | | |
|---|---|---|
| JP | 2002-519121 | 7/2002 |
| WO | WO 99/62403 A1 | 12/1999 |

OTHER PUBLICATIONS

International Search Report dated Nov. 22, 2011; International Application No. 11179079.6.

(Continued)

*Primary Examiner* — Nicholas Lucchesi
*Assistant Examiner* — Pritesh Patel
(74) *Attorney, Agent, or Firm* — Verne E. Kreger, Jr.

(57) ABSTRACT

Disclosed is a patient monitoring and drug delivery system and associated methods for use during diagnostic, surgical or other medical procedures. The functionality of the invention enables many time consuming and laborious activities to be minimized or moved to a part in the procedure where time is not as critical. The invention is capable of increasing practice efficiency in patient care facilities through system architecture and design into two separate units. A patient unit receives input signals from patient monitoring connections and outputs the signals to a procedure unit. The procedure unit is operational during the medical procedure and controls the delivery of drugs to the patient.

8 Claims, 17 Drawing Sheets

(56) References Cited

U.S. PATENT DOCUMENTS

| | | | |
|---|---|---|---|
| 5,640,953 A * | 6/1997 | Bishop et al. | 600/300 |
| 5,679,245 A | 10/1997 | Manica | |
| 5,724,025 A | 3/1998 | Tavori | |
| 5,957,885 A | 9/1999 | Bollish et al. | |
| 5,980,501 A | 11/1999 | Gray | |
| 6,302,844 B1 | 10/2001 | Walker et al. | |
| 6,406,426 B1 | 6/2002 | Reuss et al. | |
| 6,453,195 B1 | 9/2002 | Thompson | |
| 6,533,723 B1 | 3/2003 | Lockery et al. | |
| 6,651,652 B1 | 11/2003 | Ward | |
| 6,675,801 B2 | 1/2004 | Wallace et al. | |
| 6,723,086 B2 | 4/2004 | Bassuk et al. | |
| 6,745,764 B2 * | 6/2004 | Hickle | 128/203.12 |
| 6,807,965 B1 | 10/2004 | Hickle | |
| 7,152,604 B2 | 12/2006 | Hickle et al. | |
| 7,299,981 B2 | 11/2007 | Hickle et al. | |
| 7,833,213 B2 * | 11/2010 | Katz et al. | 604/500 |
| 2002/0133196 A1 | 9/2002 | Thompson | |
| 2002/0148470 A1 | 10/2002 | Blue et al. | |
| 2003/0135087 A1 | 7/2003 | Hickle et al. | |

OTHER PUBLICATIONS

International Search Report dated May 31, 2006; International Application No. PCT/US2004/06458.

European Search Report dated Apr. 29, 2009; Application No. 04716930.5.

\* cited by examiner

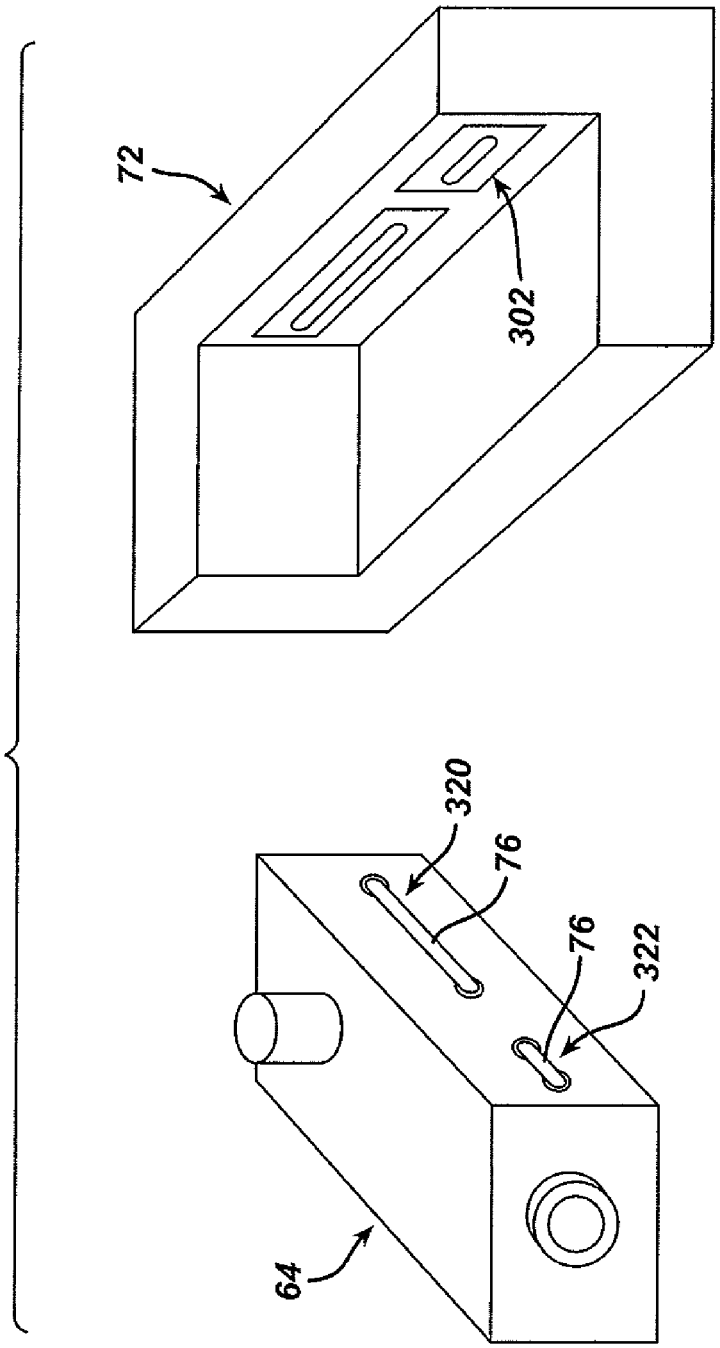

PATIENT MONITORING AND DRUG DELIVERY SYSTEM AND METHOD OF USE

CROSS REFERENCE TO RELATED APPLICATION

This application is a continuation of U.S. patent application Ser. No. 10/791,959 filed on Mar. 3, 2004, issued as U.S. Pat. No. 7,833,213, and claims the benefit and priority from U.S. provisional application, Ser. No. 60/451,860, filed on Mar. 4, 2003, the contents of which are incorporated by reference herein in its entirety.

FIELD OF THE INVENTION

The present invention relates in general to patient monitoring and drug delivery systems, and more particularly, to methods and apparatus for providing increased practice efficiency throughout medical procedures.

BACKGROUND OF THE INVENTION

Patient monitoring systems are typically used to monitor physiological parameters of patients undergoing diagnostic or surgical procedures. A variety of patient monitoring systems have been employed for the sole purpose of monitoring a patient under the influence of analgesic or amnestic drugs that are administered during painful or anxiety-causing procedures. A monitoring system capable of accurately and reliably monitoring a patient as well as being easy to use is desired.

Unfortunately, known monitoring system suffer from several disadvantages. Monitoring systems in the related art fall generally into two categories: high end, multi-function monitors which collect a multitude of data and are typically used in the procedure, and smaller, limited function monitors which gather only basic physiological data that are typically used in pre-procedure and recovery areas. Inefficiencies occur when the patient must be disconnected from one monitoring system and then, once in the procedure room, connected to a more robust monitoring system that will provide additional critical information during a surgical procedure. The process of connecting and disconnecting multiple physiological data acquisition probes from the patient causes practice inefficiencies by adding time consuming activities, resulting in an overall lengthier medical or surgical procedure.

A patient care system that increases practice efficiency is needed in many patient care facilities. A patient care facility desires to maximize efficiency and perform as many cases as safely possible in a given day. Many patient care facilities find the largest obstacle to increasing practice efficiency relates to minimizing the amount of clinician time that is required in the procedure room. The number of cases a doctor may perform in a given day is limited in part to the amount of time the patient is in the procedure room. The amount of time required to complete a particular procedure is somewhat fixed and based upon the skill and experience level of the clinician. However, much can be done to improve upon clinic practice pre-procedure and post procedure.

Typically in a pre-procedure room, a nurse or technician prepares the patient for the upcoming procedure. This preparation may include connecting monitors to the patient for the purpose of obtaining baseline data to be used in the procedure. Monitors that are commonly used include blood pressure (systolic, diastolic, and mean arterial pressure), and pulse oximetry, which measures a patient's arterial oxygen saturation and heart rate typically via an infrared diffusion sensor. Blood pressure readings are generally taken by a blood pressure cuff. A nurse or technician must secure the cuff around a patients arm and use a bulb type device to pump air into the cuff. Once the reading from the cuff stabilizes, the nurse or technician must manually record the data, usually handwritten on a sheet of paper, and save this information for later reference during the procedure and eventually, for the patient report. For the nurse or technician to take a pulse oximeter reading, he or she must boot up the pulse oximeter module, secure a pulse oximeter probe upon the patient and take a reading of the patient. This reading is also written down on paper to be saved for later use. Once it is determined the patient is ready for the procedure, the nurse or technician must disengage the blood pressure cuff and pulse oximetry probes from the patient, so the patient can be transported from the pre-procedure room to the procedure room.

After the patient enters the procedure room and before the procedure may begin, several tasks are needed to prepare the patient for the procedure. The nurse or technician must reconnect both blood pressure and, pulse oximetry before the procedure can begin. In addition to blood pressure and pulse oximetry other connections such as, for example, capnography, supplemental oxygen, and electrocardiogram are required. A great deal of time is required to connect the physiological monitors to the patient and to connect the physiological monitors to the monitoring system. The nurse or technician must spend time reconnecting physiological monitors that were connected to the patient in the pre-procedure room. The time it takes to make these connections occupies valuable procedure room time, thus decreasing practice efficiency. Clearly a need exists to minimize or eliminate these monitor connections and reconnections while their patient is in the procedure MOM.

Besides the time delays which may be encountered when adding sensors to the monitors, monitoring systems in the prior art leave much to be desired with respect to cable management. A large number of cables extend between the patient and the monitor. In the past there has been at least one cable for every parameter monitored. This array of cables and hoses interferes with the movement of personnel around the patient's bed. The greater the number of cables and hoses, the greater the risk that someone will accidentally disrupt one of them. In the course of a procedure, many people including nurses, technicians, and physicians must be able to move around the room and access the patient without, having to navigate around cables. This invention addresses cable management, by minimizing the number of cables between patient and monitor.

An additional focus of this invention is the use of fast acting analgesic or amnestic drugs to decrease the length of most procedures and the time needed to recover from procedures, thus increasing practice efficiency. Current solutions for providing patient relief from pain and anxiety require the use of drugs that require a relatively long time to take peak effect and, take a relatively long time for the effect to pass from patient. Physicians must wait for drugs to take full effect for the procedure to begin. The time spent waiting for the drug to take affect is wasted time that hinders practice efficiency. This invention provides means for safely and reliably delivering fast acting drugs in an effort to increase practice efficiency.

An additional focus of this invention is to automate several functions currently performed by clinicians to increase practice efficiency. In current practice, prior to IV drug delivery, nurses must manually purge the IV line of any air that may be trapped in the line before connecting the line to a patient. Failure to do so will result in harmful effect on the patient from air entering the patient's blood stream. The process of purging this line takes a significant amount of time and hinders practice efficiency. This invention provides means for automating the line purging process.

DESCRIPTION OF THE DRAWING

Other objects and many of the intended advantages of the invention will be readily appreciated as they become better understood by reference to the following detailed description of embodiments of the invention considered in connection with the accompanying drawings, wherein:

FIG. 3-A is a perspective view of an alternate embodiment of a patient unit.

FIG. 3-B is a perspective view of the patient unit of FIG. 3-A connected to a procedure unit.

FIG. 3-C is an exploded view of the patient unit of FIG. 3-A.

FIG. 3-D is a perspective view of the patient unit of FIG. 3-A illustrating the cable connection and bedside connection.

FIG. 3-E is exploded view of an alternate embodiment of the patient unit of FIG. 3-A.

FIG. 4-A is a flow diagram depicting the auto priming aspect of the invention.

FIG. 4-B is a partial cut-away view of a drug cassette for use with the procedure unit.

FIG. 4-C is a perspective view of an alternate embodiment of a drug cassette and pump module for use with the procedure unit.

SUMMARY OF THE INVENTION

Figure 1:
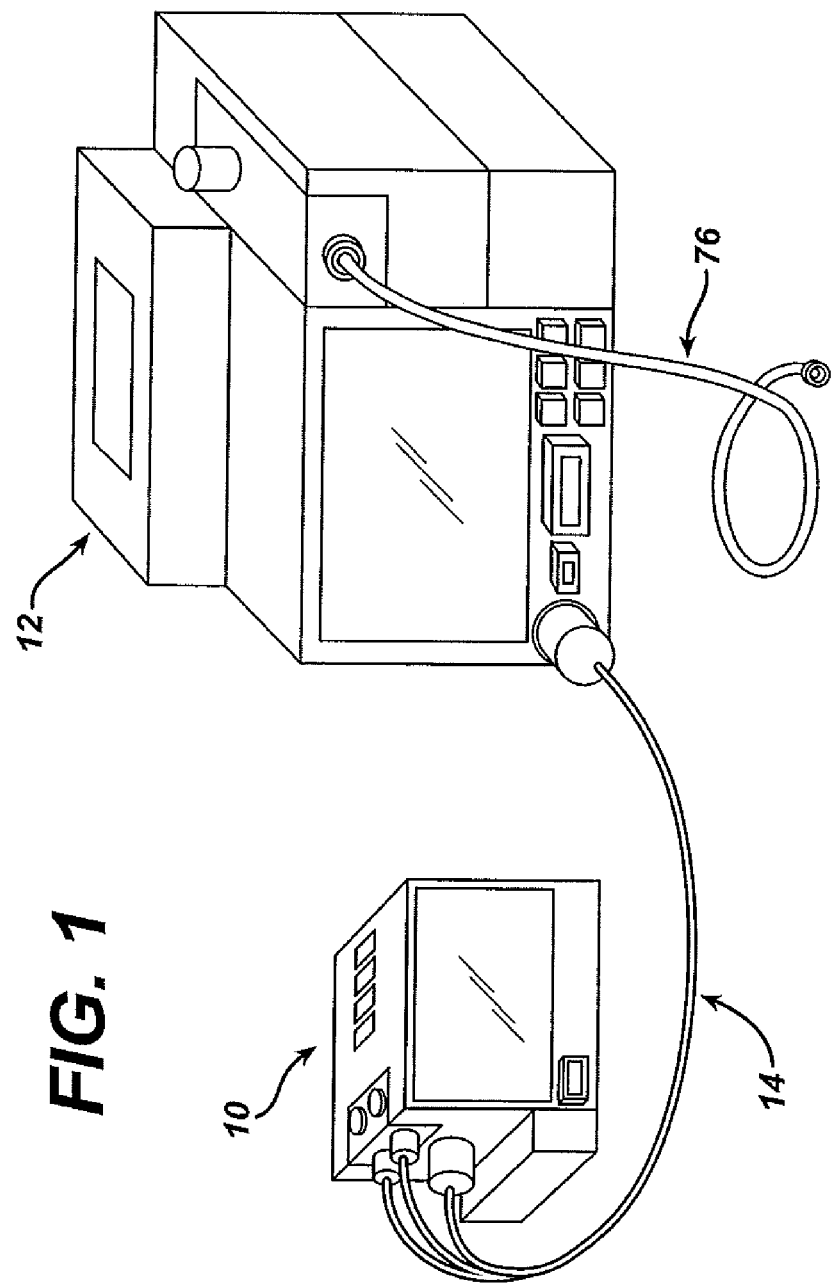
FIG. 1 is a perspective view of a one embodiment of a care system apparatus constructed in accordance with this invention, depicting a bedside or patient unit and a procedure unit.

The invention provides apparatuses and methods to efficiently deliver a pharmaceutical drug, for example and not limited to, a sedative, analgesic or amnestic drug, to a patient during a medical procedure as exemplarily described in U.S. patent publications US2002/0017296, US2002/0017300 and US2002/0188259.

The functionality of the invention allows for, but is not limited to, enabling many time consuming and laborious activities to be minimized or moved to a part in the procedure where time is not as critical. To these ends, the invention is capable of physically separating through system architecture and design into two separate monitoring units which, when used as described herein, will increase practice efficiency in patient care facilities.

In general, the invention is a micro-processor based patient monitoring system and drug delivery system having a patient unit that receives input signals from patient monitoring connections. The patient unit outputs patient parameters to a procedure unit and also includes a display screen for displaying patient parameters. The procedure unit is operational during the medical procedure and receives patient parameters from the patient unit. The procedure unit controls the delivery of drugs to the patient.

An additional aspect of this invention is directed to the facilitation of creating a patient record of the procedure. Current techniques for creating a patient record involve manual note taking by a nurse during the course of a patients stay. This technique is time consuming and may lead to errors in record keeping. This invention provides mean for monitoring patient parameters throughout a procedure, electronically capturing data and giving the nurse or technician the option of printing a copy of this data for the purpose of record keeping.

A further aspect of this invention is a method for monitoring a patient and delivering at least one drug during a medical procedure that comprises the steps of connecting to the patient at least one sensor for monitoring at least one physiological parameter of the patient; providing a microprocessor-based patient unit having at least one first connection point and receiving input signals from the at least one sensor through the at least one first connection point and at least one second connection point for outputting patient physiological parameters; inputting to the patient unit physical attributes of the patient; and creating a patient record.

A further expression of the method for monitoring a patient and delivering at least one drug during a medical procedure includes connecting the at least one second connection point to a micro processor-based procedure unit; connecting a drug cassette containing a drug vial to an infusion pump; delivering the drug to the patient and performing a medical procedure; and disconnecting the at least one second connection point from the procedure unit.

A still further expression of the method includes monitoring the at least one physiological condition of the patient; disconnecting the input signals from the at least one sensor from the at least one first connection point; and terminating the creation of the patient record.

Other focuses of the invention are apparent from the below detailed description of preferred embodiments.

Detailed Description of the Preferred Embodiments

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described embodiments, expressions of embodiments, examples, methods, etc. can be combined with any one or more of the other following-described embodiments, expressions of embodiments, examples, methods, etc.

Figure 6:
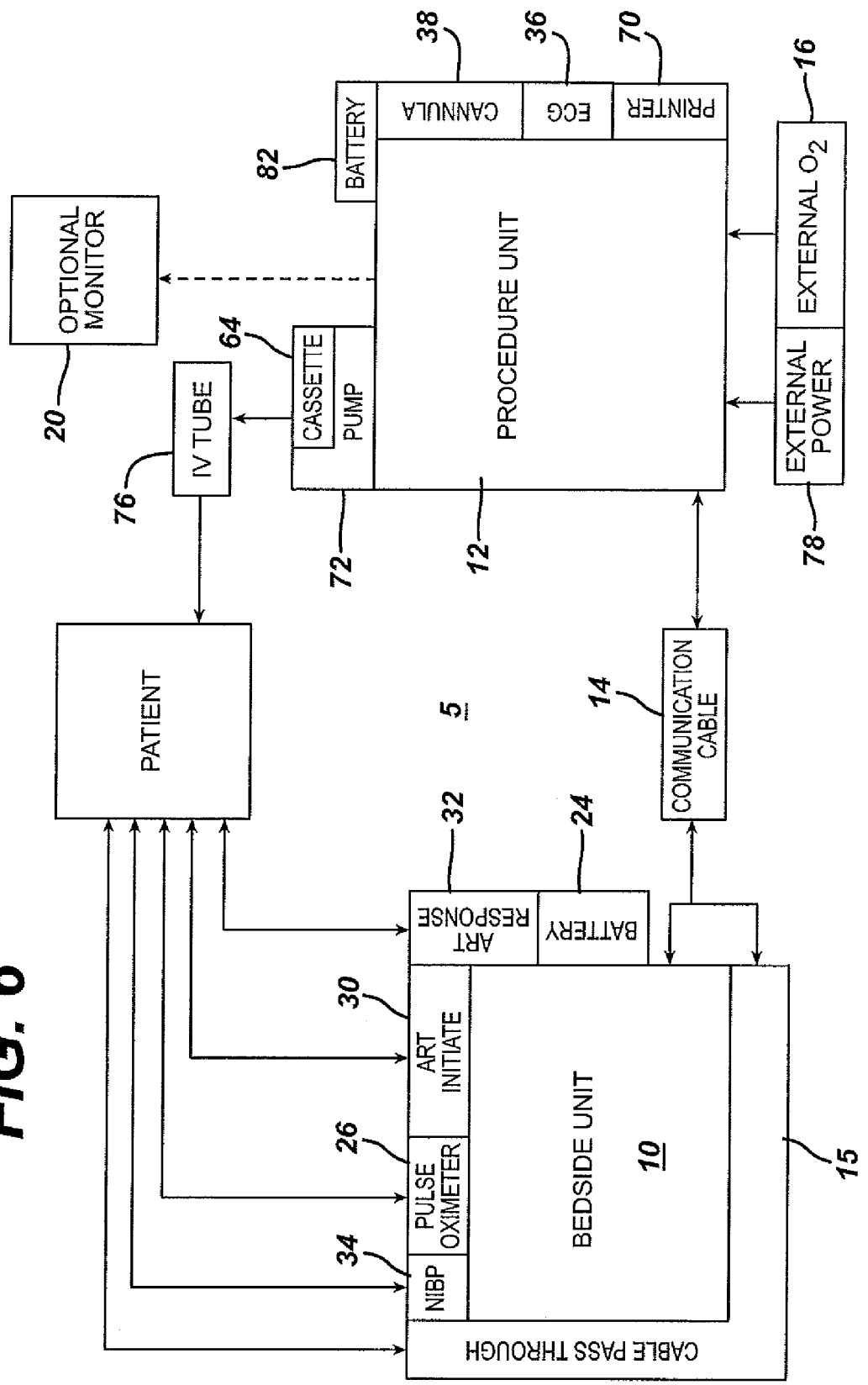
FIG. 6 is a block diagram overview of the invention.

The system block diagram of FIG. 6 depicts the system architecture of one embodiment of the invention. This diagram illustrates the relationships between the components of a patient care system 5, which are described in more detail below. Procedure unit 12 has several integrated components including ECG module 36, cannula module 38, battery 82 and peristaltic infusion pump 72. External oxygen 16 and external power 78 are not integrated into procedure unit 12 however; they do have connections to procedure unit 12. Peristaltic infusion pump 72 interfaces with drug cassette 64 to pump analgesic or sedative drugs. These analgesic or sedative drugs are then pumped through IV tubing 76 and into the patient. In addition to the displays incorporated into bedside unit 10 and procedure unit 12, an optional display 20 is available for use by the clinician, and could display information such as, for example, patient physiological parameters and, warning alarms. Procedure unit 12 may use a wireless transmitter device such as, for example, "Blue Tooth" to send signals to a wireless receiver device located on optional display 20. Communication cable 14 serves as a data link between procedure unit 12 and bedside unit 10. Bedside unit 10 has a plurality of integrated devices including, NIBP module 34, pulse oximeter module 26, ART modules 30, 32, and bedside unit battery 24. Bedside unit 10 allows for several connections between bedside unit 10 and the patient being monitored including but not limited to oral nasal cannula 48, ECG pads 50, NIBP cuff 58, pulse oximeter probe 60, ART earpiece 55, and ART handpiece 57. Bedside unit 10 is designed to function independent of, or connected to procedure unit 12.

As shown in FIG. 1, patient care system 5 comprises two monitoring units; a bedside unit 10 and a procedure unit 12. One exemplary use of patient care system 5 is to monitor patient parameters and deliver sedative, analgesic and/or amnestic drugs to a conscious, non-intubated, spontaneously-ventilating patient undergoing a diagnostic or surgical procedure by a physician. This use is not exhaustive of all of the potential uses of the invention but will be used to describe the invention.

Bedside unit 10 and procedure unit 12 are connected via communication cable 14. Communication cable 14 provides means for transmitting electronic data as well as various hydraulic signals and gases between beside unit 10 and procedure unit 12. Communication cable 14 may be removed from both bedside unit 10 and procedure unit 12 to facilitate practice efficiency and user convenience. Bedside unit 10 and procedure unit 12 are free to move independently of each other if communication cable 14 is not in place. This allows for mobility of each unit independent of the other; this feature is especially important in hospitals that have a great deal of medical procedures and there is little time to connect patients to monitors. Bedside unit 10 and procedure unit 12 preferably accommodate an external oxygen source that is intended to provide supplemental oxygen to the patient during the course of a surgical procedure if the clinician so desires. An IV tube set 76 is shown connected to procedure unit 12 and delivers sedative or amnestic drugs to a patient during a surgical procedure.

Figure 2:
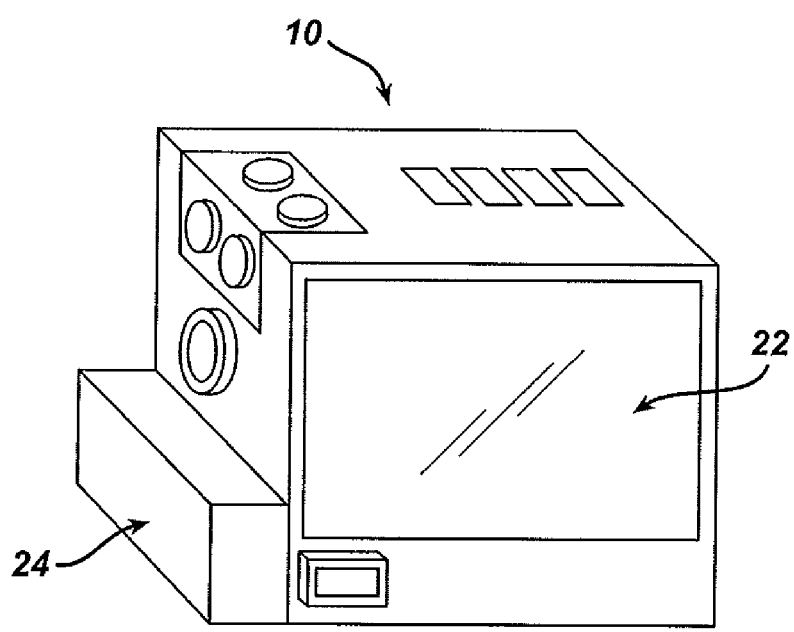
FIG. 2 is a perspective view of an embodiment of a care system apparatus constructed in accordance with this invention depicting a mobile patient unit.

As shown in FIG. 2, beside unit 10 is compact and portable so it requires little effort to move from one room to another. In the one embodiment, bedside unit 10 could mount upon either an IV pole or a bedrail; this would free the clinician from the burden of carrying the unit wherever the patient needs to be transported. Bedside unit 10 is small and light enough to be held in the hand of a nurse or technician. Bedside unit 10 allows the user to input information via the bedside touch screen assembly or a simple keypad 22. Bedside touch screen assembly 22 is a display device that is integrated into one surface of bedside unit 10, and displays patient and system parameters, and operational status of the apparatus. An exemplary bedside touch screen assembly 22 is a 5.25" resistive touch screen manufactured by MicroTech mounted upon a 5.25" color LCD manufactured by Samsung. An attending nurse or physician may enter patient information such as, for example, patient weight and a drug dose profile into bedside unit 10 by means of bedside touch screen assembly 22. Bedside unit battery 24 is fixedly attached to the bedside unit 10 and is a standard rechargeable battery such as, for example, Panasonic model no. LC-T122PU, that is capable of supplying sufficient power to run bedside unit 10 for an extended period of time. In one embodiment, bedside unit battery 24 can be recharged while bedside unit 10 is connected to procedure unit 12 via communication cable 14 or can be charged directly from an independent power source.

Figure 3:
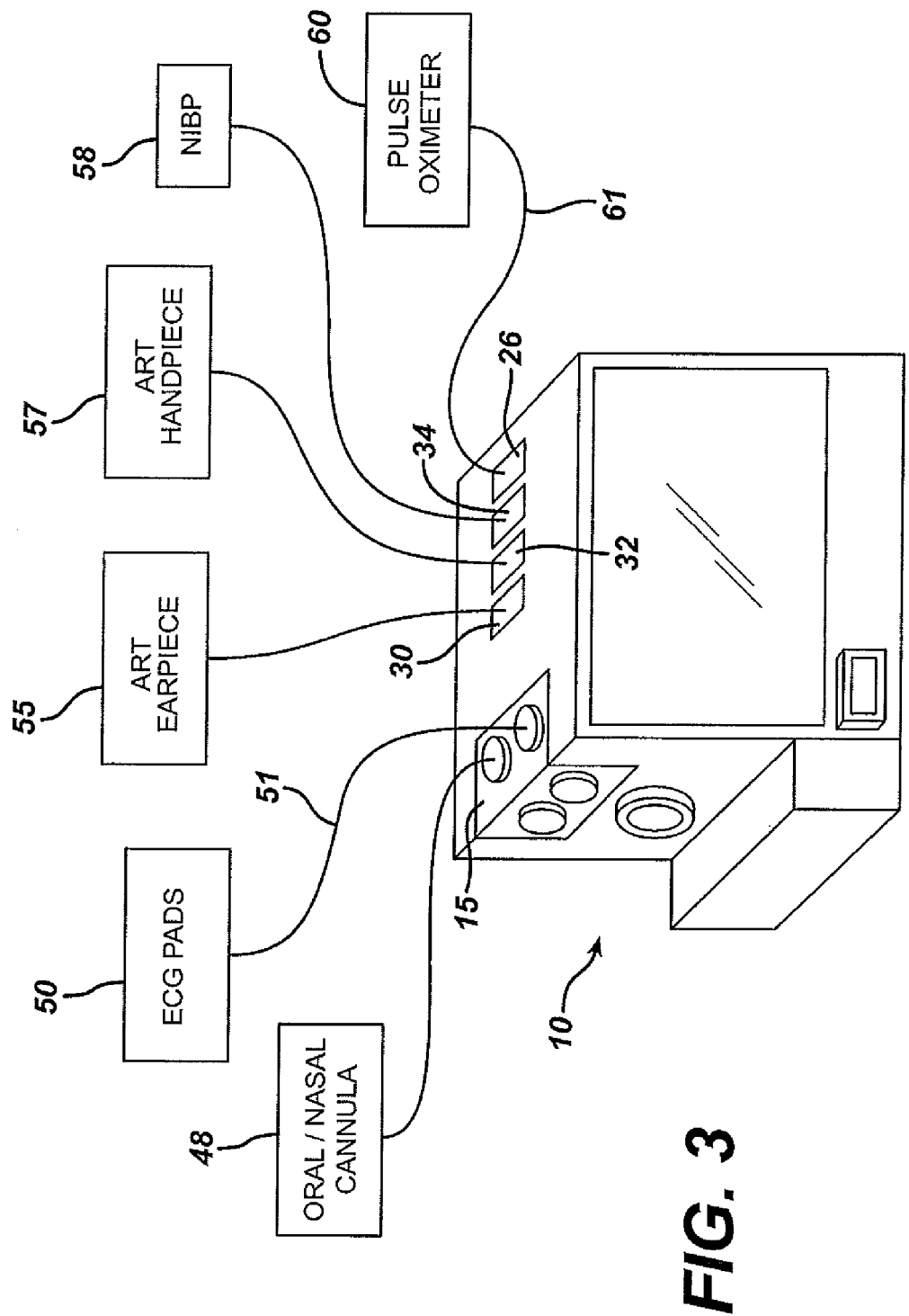
FIG. 3 is a perspective view of an embodiment of a care system apparatus constructed in accordance with this invention depicting the patient unit connected with various patient sensors, and other patient interfaces.
Figure 3A:
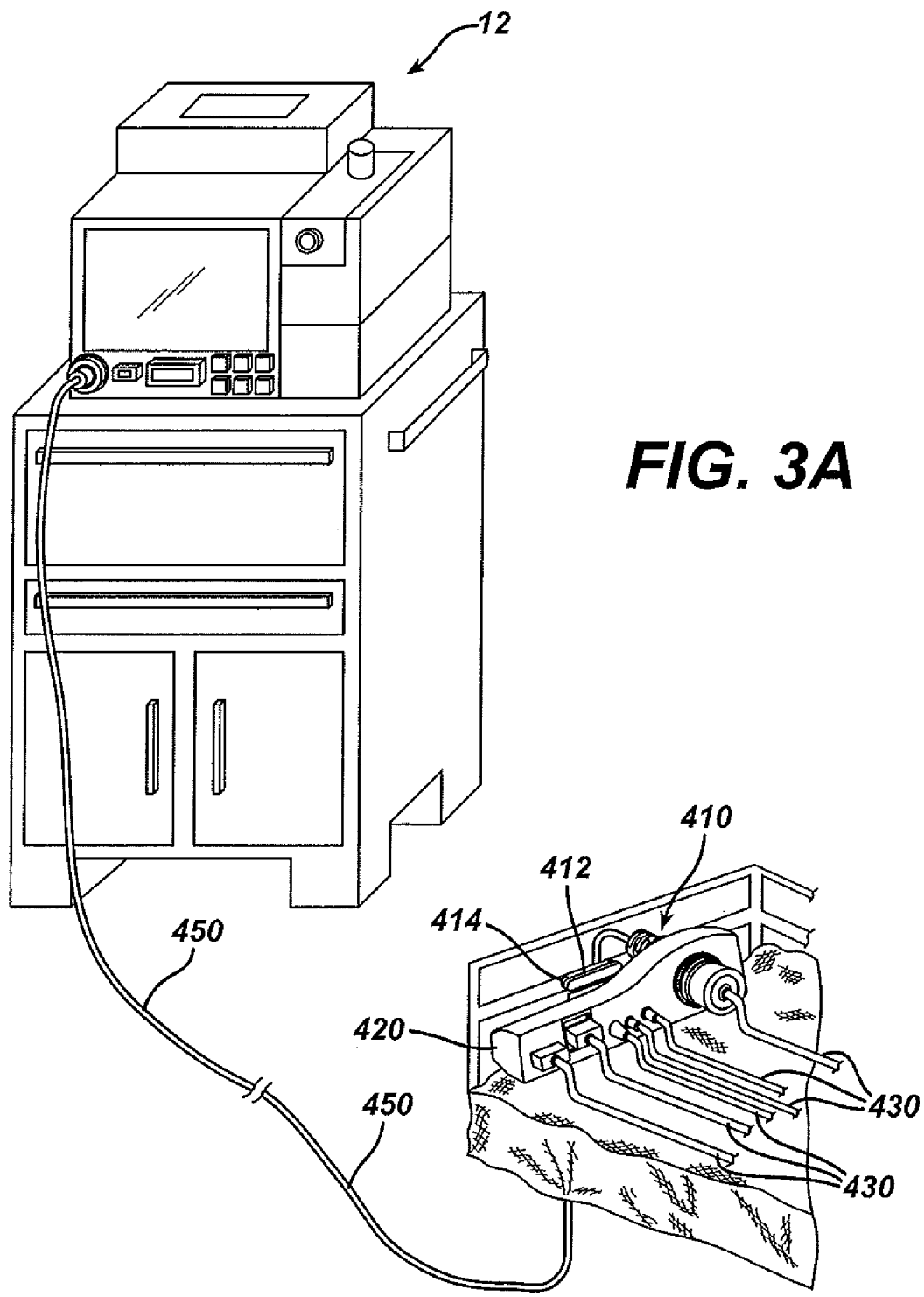
Figure 3B:
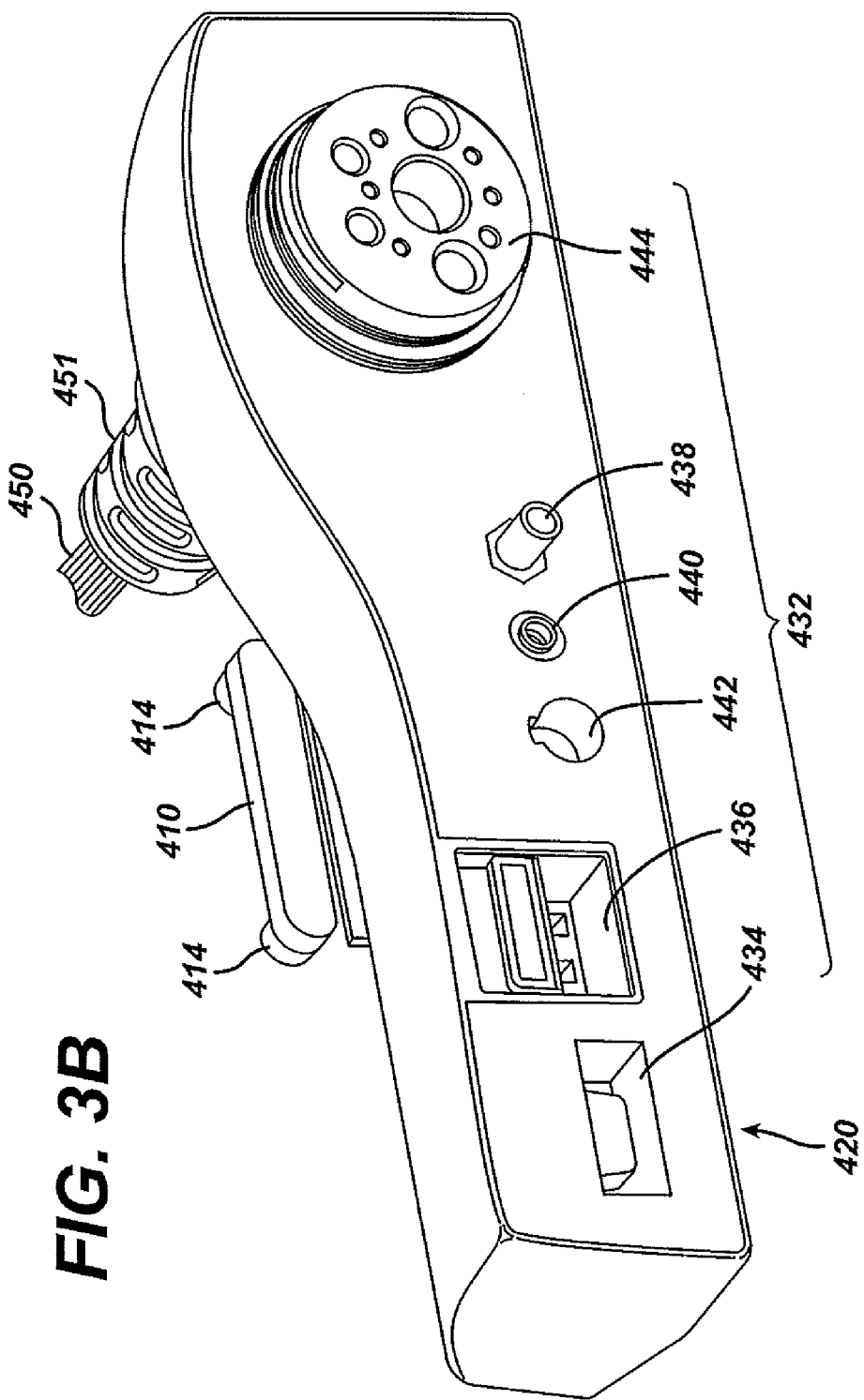
Figure 3C:
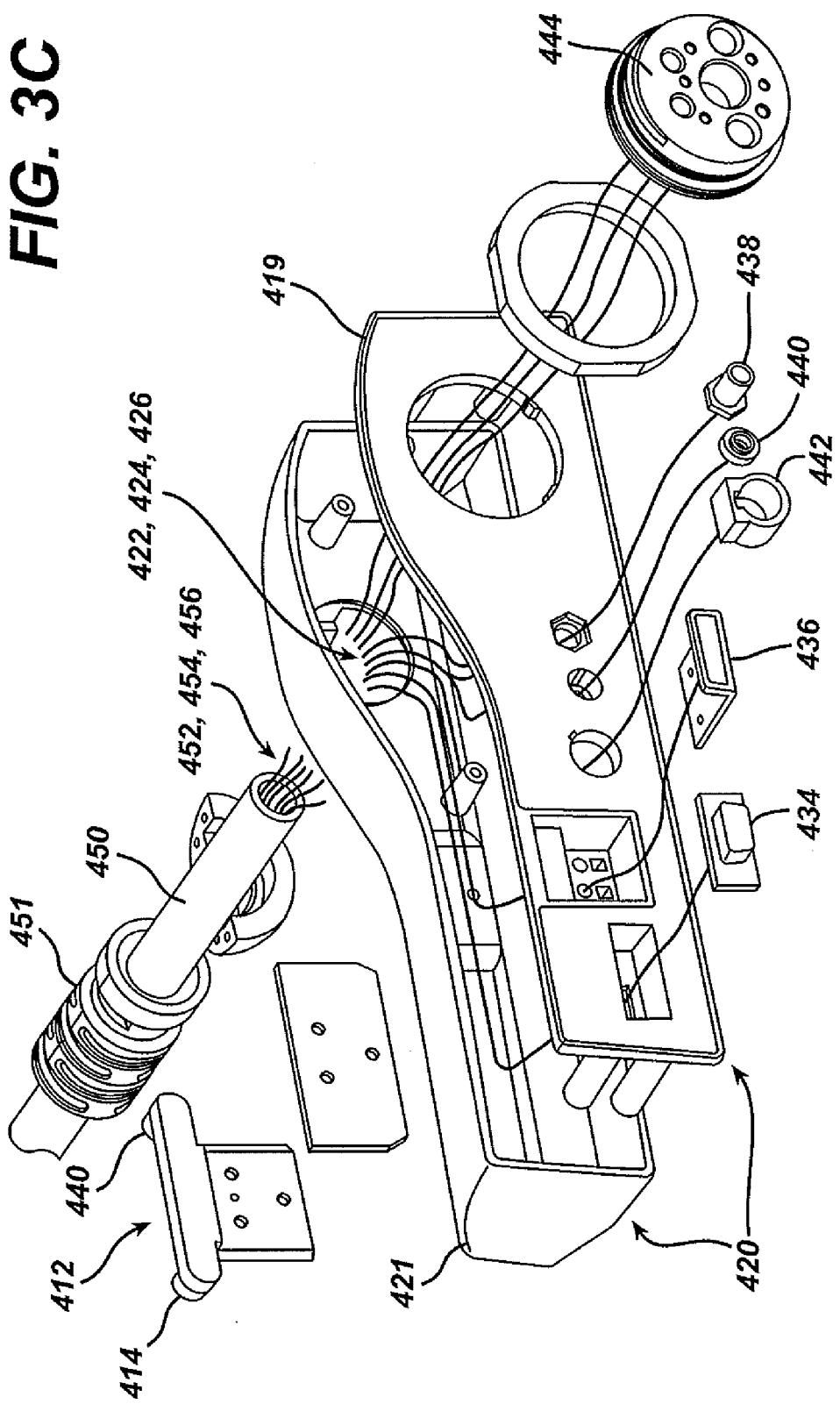
Figure 3D:
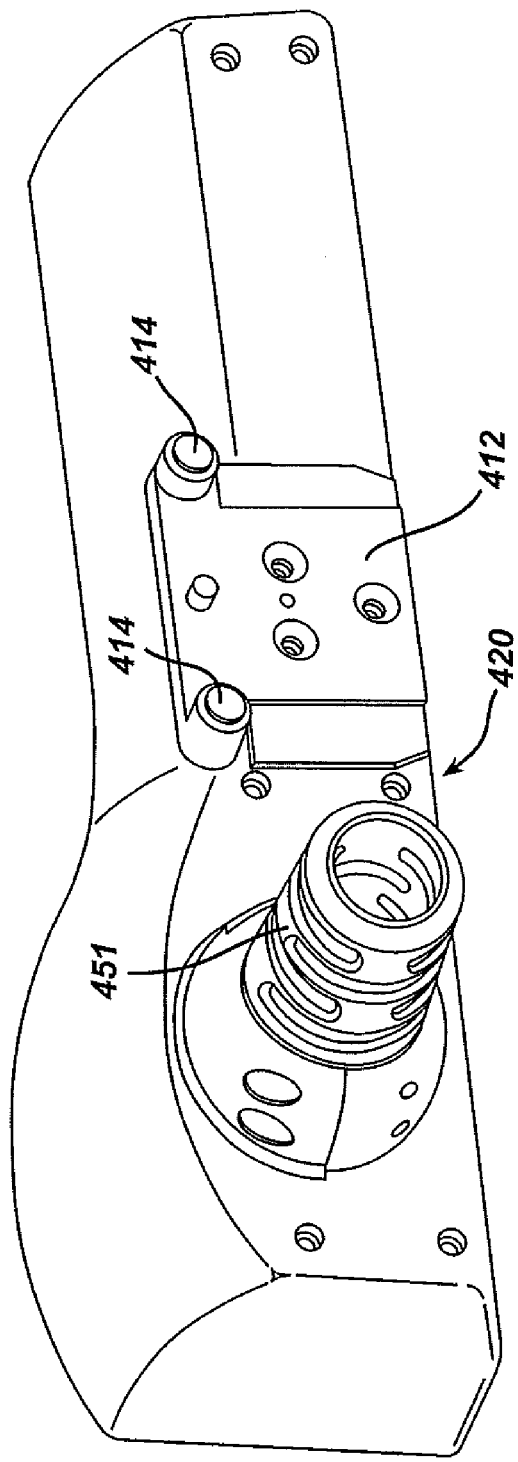
Figure 3E:
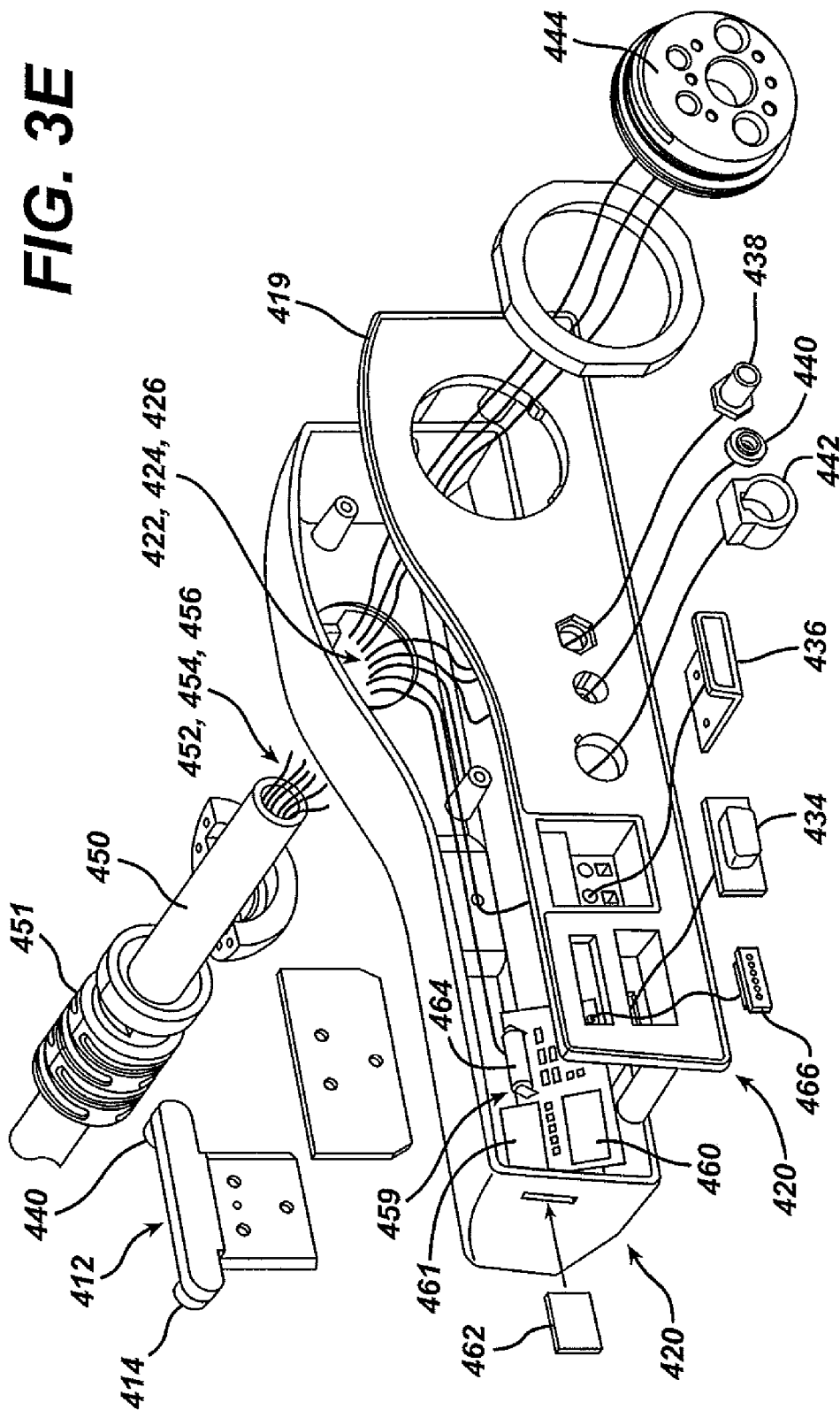

As shown in FIG. 3 bedside unit 10 may be connected to a plurality of patient sensors and peripherals used to monitor patient vital signs and deliver supplemental oxygen to the patient. One aspect of the invention integrates drug delivery with one or more basic patient monitoring systems. These systems interface with the patient and obtain electronic feedback information regarding the patient's physiological condition. Oral nasal cannula 48 delivers oxygen from an external oxygen source and collects samples of exhaled gas. Oral nasal cannula 48 is removably attached to cable pass-through connection 15. Cable pass-through connection 15 sends the signal obtained by oral nasal cannula 48 directly to a capnometer (e.g., a CardioPulmonary Technologies CO2WFA OEM) in procedure unit 12 and preferably via communication cable 14 (FIG. 1). The capnometer measures the carbon dioxide levels in a patient's inhalation/exhalation stream via a carbon dioxide-sensor as well as measuring respiration rate. Also attached to the cable pass-through connection 15 is a standard electrocardiogram (ECG) 50, which monitors the electrical activity in a patient's cardiac cycle. The ECG signals are sent to the procedure unit 12 where the signals are processed.

Also connect to bedside unit 10 is a pulse oximeter probe 60 (e.g., Dolphin Medical) and a non-invasive blood pressure (NIBP) cuff 58. Pulse oximeter probe 60 measures a patient's arterial saturation and heart rate via an infrared diffusion sensor. The data retrieved by pulse oximeter probe 60 is relayed to pulse oximeter module 26 (e.g., Dolphin Medical) by means of Pulse Oximeter Cable 61. The non-invasive blood pressure (NIBP) cuff 58 (e.g., a SunTech Medical Instruments PN 92-0011-00) measures a patient's systolic, diastolic and mean arterial blood pressure by means of an inflatable cuff and air pump (e.g., SunTech Medical), also incorporated as needed. NIBP cuff 58 is removably attached to NIBP module 34 located on bedside unit 10.

A patient's level of consciousness is detected by means of an Automated Response Tester System (ART). An exemplary ART system is disclosed in U.S. patent application Ser. No. 10/674,160 and filed on Sep. 29, 2003, which is incorporated by reference herein. The ART system comprises a query initiate device and a query response device. The ART system operates by obtaining the patient's attention with the query initiate device and commanding the patient to activate the query response device. The query initiate device may be any type of stimulus such as a speaker via an earpiece 55, which provides an auditory command to a patient to activate the query response device. The query response device is a handpiece 57 that can take the form of, for example, a toggle or rocker switch or a depressible button or other moveable member hand held or otherwise accessible to the patient so that the member can be moved or depressed by the patient upon the patient's receiving the auditory or other instruction to respond. Alternatively, a vibrating mechanism may be incorporated into the handpiece 57 that cues the patient to activate the query response device. In one embodiment, the query initiate device is a cylindrical handheld device 57, containing a small 12V dc bi-directional motor enabling the handheld device to vibrate the patient's hand to solicit a response.

After the query is initiated, the ART system generates signals to reflect the amount of time it took for the patient to activate the query response device in response to the query initiate device. These signals are processed by the main logic board located inside bedside unit 10 and are displayed upon either bedside touch screen assembly 22, procedure touch screen assembly 62 (FIG. 4) or an optional monitor 20 (FIG. 6). The amount of time needed for the patient to respond to the query gives the clinician an idea as to the sedation level of the patient. The ART System has two modules, the query response module 32 and the query initiate module 30, collectively referred to as the ART system modules 30,32. ART system modules 30,32 have all the necessary hardware to operate and connect the query response device 57 and the query initiate device 55 to bedside unit 10.

In one embodiment monitoring modules 26, 30, 32, and 34 are easily replaceable with other monitoring modules in the event of malfunction or technological advancement. These modules include all the necessary hardware to operate their respective peripherals. The above-mentioned patient modules are connected to a microprocessor-based electronic controller or computer (sometimes also referred to herein as main logic board, MLB) located within each of the procedure unit 12 and bedside unit 10. The electronic controller or main logic board comprises a combination of available programmable-type microprocessors and other "chips," memory devices and logic devices on various board(s) such as, for example, those manufactured by Texas Instruments (e.g., XK21E) and National Semiconductor (e.g., HKL72), among others.

Once bedside unit 10 and procedure unit 12 are connected via communication cable 14, ECG and capnography will be monitored, and supplemental oxygen will be delivered to the patient. Preferably, however, these connections are made in the pre-procedure room to increase practice efficiency. By making these connections in the pre-procedure room, less time is required in the procedure room connecting capnography, ECG and supplemental oxygen to procedure unit 12. Oral nasal cannula 48 and ECG leads 51 are connected directly to cable pass-through connection 15. Cable pass-through connection 15, located on bedside unit 10, is essentially an extension of communication cable 14, which allows the signals from ECG leads 51 and oral nasal cannula 48 to bypass bedside unit 10 and be transferred directly to procedure unit 12. It will be evident to those skilled in the art, however, that the bedside unit 10 could be configured to accept the ECG 50 and oral/nasal cannula 48 signals and process the signals accordingly to provide the information on screen 22 and supplemental oxygen to the patient in the pre-procedure room. As more features are added to the bedside unit 10, however, the portability may be limited.

Referring now to FIG. 3-A there is shown a console assembly 410 of the present invention in connection with procedure unit 12. In this embodiment, console assembly is a simpler version of the bedside unit 10. As used herein, the term "proximal" refers to a location on the console assembly 410 closest to the device using the console assembly 410 and thus furthest from the patient connected to the console assembly 410. The term "distal" refers to a location farthest from the device using the console assembly 410 and closest to the patient.

As illustrated in FIGS. 3A-D, console assembly 410 comprises mounting 412, console box 420, and console connector cable 450. Mounting 412 allows console assembly 410 to easily mount horizontally or vertically on, for example a patient's bed rail or IV pole, and is preferably made of a rigid thermoplastic such as, for example, polycarbonate. Mounting 412 is attached to the proximal end of Console Box 420 and includes mounting posts 414 thereon. Mounting posts 414 help secure mounting 412 on a patient's bed rail or IV pole.

Console box 420, with an outer casing preferably made of a rigid thermoplastic such as, for example, polycarbonate, includes faceplate 419 and hub 421. Faceplate 419 can be fixedly attached to hub 421 using any attachment means including, but not limited to, glue, mechanical fasteners, screws, and ultrasonic welding. Console box 420 further includes receptacles 432 therein. Receptacles 432 include, but are not limited to, pulse oximeter port 434, ECG monitor port 436, NIBP monitor port 438, ART earpiece jack 440, ART handpiece port 442, and oral nasal cannula port 444 that includes supplemental oxygen delivery. Receptacles 432 can be standard medical device connections, well known in the medical art, or custom device connections for use with medical devices custom designed to connect to console box 420. Console box 420 further includes a plurality of electrical wires 422, air lines 424 and oxygen delivery tubes 426 therein which connect from the respective receptacle 432 through console box 420 and to corresponding wires 452, tubes 454 and power lines 456 in connector cable 450.

As shown in FIG. 3-A, Console assembly 410 further includes a plurality of cables 430. Cables 430, which connect to receptacles 432, attach to any number of devices during a surgical procedure to monitor a patient, among other things. These devices can include, but are not limited to, an oral nasal cannula, a blood pressure cuff, ECG leads and a pulse oximeter monitor, among others.

Connector cable 450, which is covered with insulation, such as, for example mil-ene or silicon, includes a plurality of wires 452, tubes 454 and power lines 456 that supply electrical signals, hydraulic signals, and oxygen delivery integrated into one cable and allow console box 420 to be hardwired to procedure unit 12. Connector cable 450 further includes strain relief 451 at its distal end. Strain reliefs are well known in the art and play an important role in helping to prevent flexing, which causes wires to break after prolonged use, at the connection between connector cable 450 and console box 420.

As shown in FIG. 3-E, Console box 420 further includes circuit board 459, microprocessor 460, removable flash memory reader 461, removable flash memory 462, battery 464, and at least one computer interface 466. Circuit board 459 can be a multi-layered printed circuit board. Copper circuit paths called traces that resemble a complicated roadmap carry signals and voltages across circuit board 459. Layered fabrication techniques can be used so that some layers of circuit board 459 can carry data for microprocessor 460 and removable flash memory 462 while other layers carry voltages and ground returns without the paths short-circuiting at intersections. The insulated layers can be manufactured into one complete, complex sandwich. Chips and sockets can be soldered onto circuit board 459. Mounted to circuit board 459 is microprocessor 460. Microprocessor 460 is the computational engine of the data received by console box 420 from the external monitors. Microprocessors are well known in the computer field and one of many suitable microprocessors such as, for example, a Pentium, a K6, a PowerPC, a Sparc, a Motorola Dragonball™, among others, may be used for microprocessor 460. Microprocessor 460 can be run by a software application. The software application can be written in one of many formal programming languages, which can include, but is not limited to Java, C++, Visual Basic, and Fortran. The software application and microprocessor 460 together create a data log of all the physiological parameters gathered from the patient via console box 420 and procedure unit 12. Circuit board 459 also has removable flash memory reader 461 electrically attached thereto. Removable flash memory reader 461, which includes a slot in the outer casing of console box 420, more specifically hub 421, allows removable flash memory 462 to be inserted and removed from circuit board 459. When removable flash memory 462 is inserted in removable flash memory reader 461, removable flash memory 462 is in digital communication with microprocessor 460, circuit board 459, and computer interface 466. Removable flash memory 462 is a solid-state storage device used for easy and fast information storage of the data log generated by microprocessor 460 running its corresponding software application. Removable flash memory 462 is well known in the computer field and one of the many suitable flash memory cards such as, for example, a SmartMedia Card, a MultiMedia Card, or a CompactFlash Card along with others may be used for removable flash memory 462. The data is stored so that it may be retrieved from removable flash memory 462 at a later time.

When console assembly 410 is removed from procedure unit 12 or another external monitor, battery 464, which can be comprise lithium ion, supplies power to the components in console box 420 including microprocessor 460. Microprocessor 460 along with its software application and removable flash memory 462 can digitally communicate its data through computer interface 466. Computer interface 466 can include, but is not limited to, a standard serial port, a USB port, an IEEE1394 port, a RS232 port, or an Ethernet port. Computer interface 466 sends data formatted by the software application to be printed as a patient report. In addition, removable flash memory 462 can be removed from console box 420 and inserted in one of many compatible flash memory card readers so that the data may be downloaded on a personal computer or handheld device.

During a surgical procedure using console assembly 410 of the present invention, the patient is first admitted and prepped for the procedure. During this stage, a health care clinician or surgeon connects various vital monitors such as, for example, a pulse oximeter monitor on the patient. Cables 430 associated with these monitors are connected to the respective receptacle 432 on console box 420. A patient record is then initiated through microprocessor 460 and its software application in flash memory 462 and data from the patient such as vitals from cables 430 can now be stored in flash memory 462. Next, the patient is moved to the procedure room and console assembly 410 connects to procedure unit 12 or other medical monitoring devices. Flash memory 462 continues to collect data for the patient record gathering information via microprocessor 460 from cable 430 and procedure unit 12 including, but not limited to, vital signs, drugs delivered, and other physiological parameters. After the procedure is complete console box 420 is disconnected from procedure unit 12, and the patient is moved to a recovery and discharge stage. During this stage, flash memory 462 continues to gather data from cable 430 including, but not limited to vitals and post-op drugs. When the patient is ready for discharge, flash memory 462 stops taking data and closes the patient record.

Figure 4:
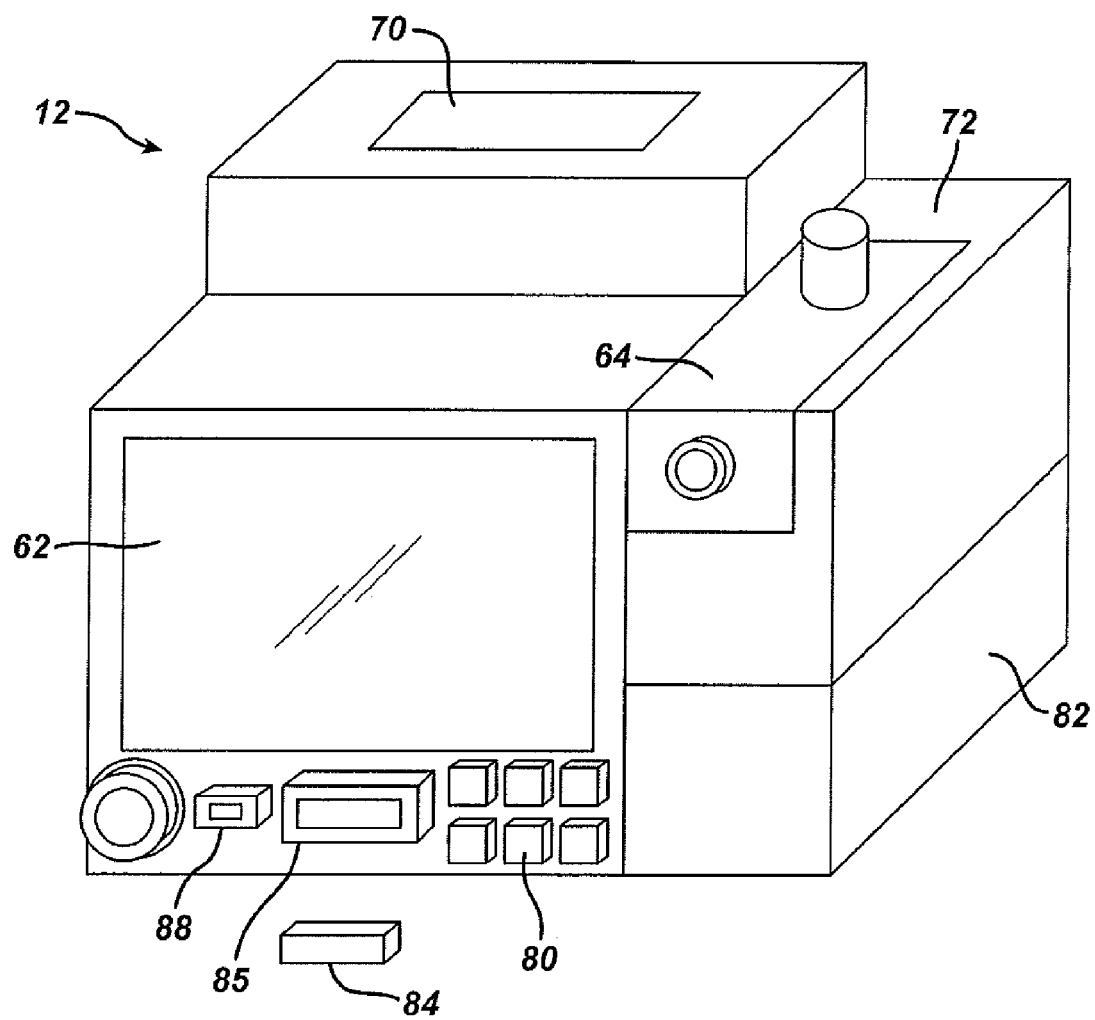
FIG. 4 is a perspective view of the procedure unit.
Figure 4A:
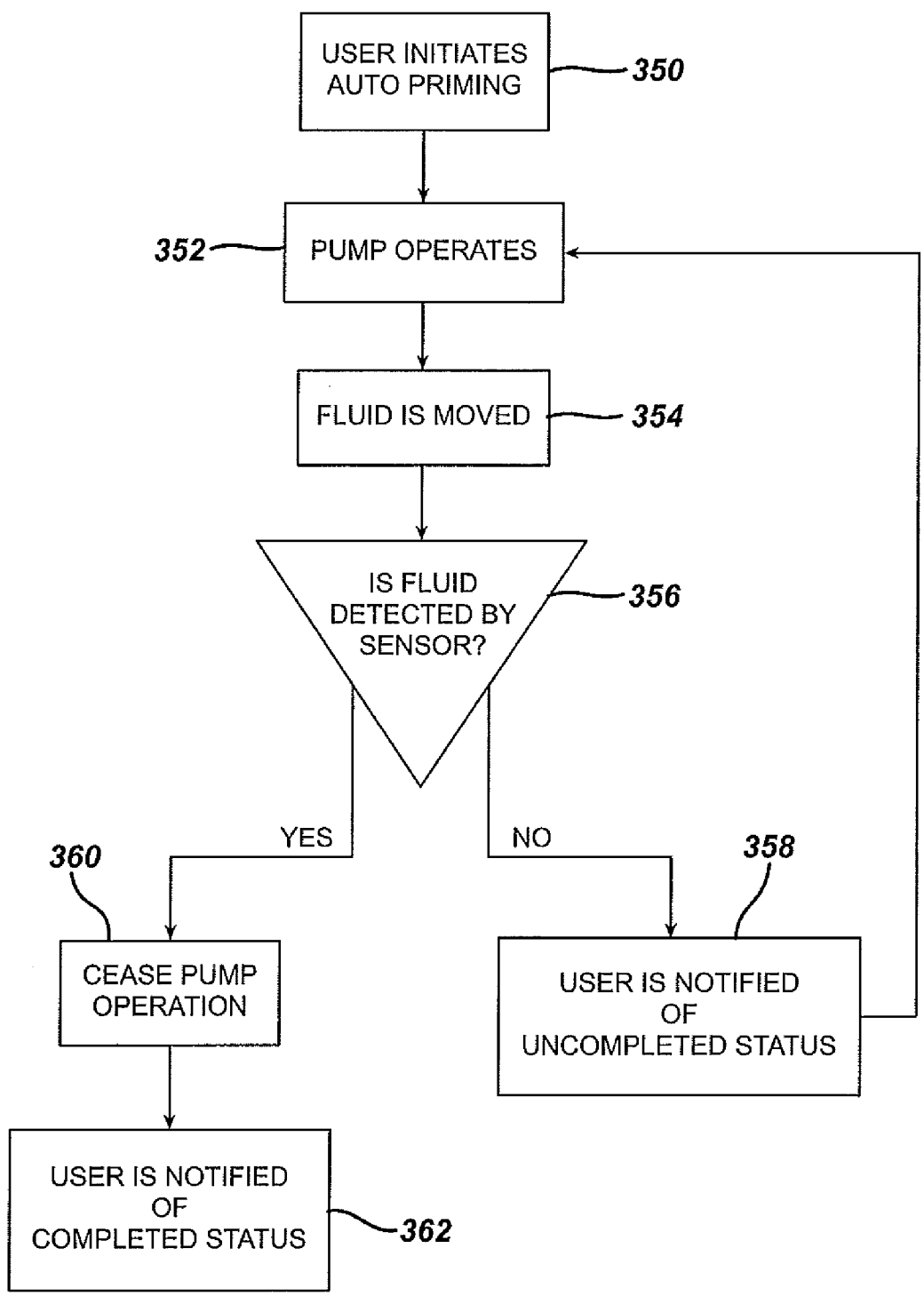
Figure 4B:
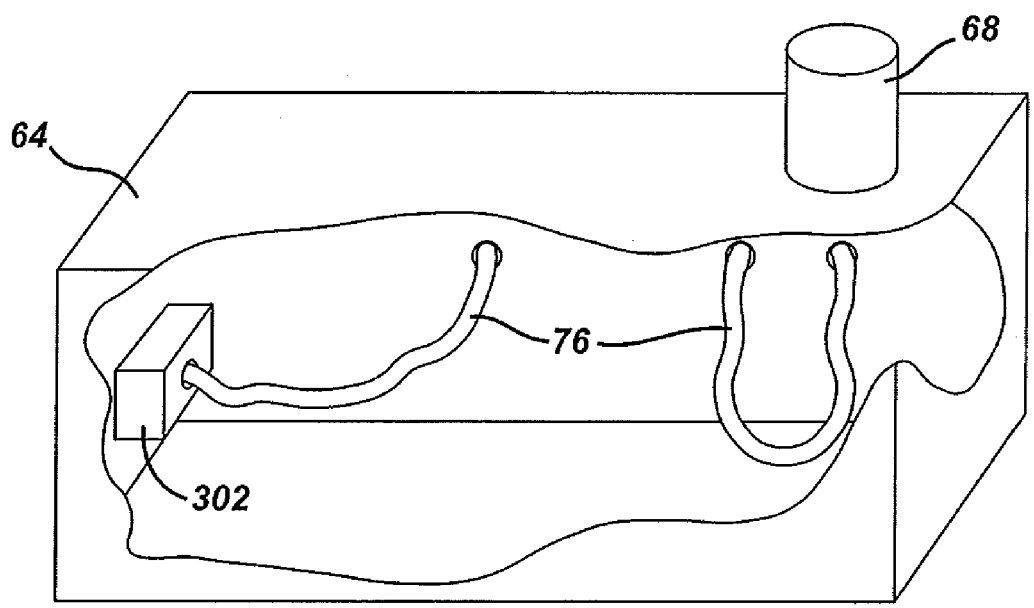

Referring now to FIG. 4, procedure unit 12 allows a physician to safely deliver drugs, such as a sedative or analgesic drug to a patient and monitor the patient during the medical procedure. Procedure touch screen assembly 62 is a display device that is integrated into the surface of procedure unit 12, which displays patient and system parameters, and operation status of the apparatus. In one embodiment, procedure touch screen assembly 62 consists of a 15" resistive touch screen manufactured by MicroTech mounted upon a 15" color LCD manufactured by Samsung. It should be noted that procedure touch screen assembly 62 is the primary display and input means, and is significantly larger than the bedside touch screen assembly 22 and capable of displaying more detailed information. In addition to procedure touch screen assembly 62, the user may input information into procedure unit 12 by means of drug delivery controls 80. Drug delivery controls 80, such as buttons or dials, are located on one side of procedure unit 12 and preferably, allow the clinician to change various system parameters and bypass procedure touch screen assembly 62. Printer 70 is integrally attached to the top of procedure unit 12. Printer 70 allows the clinician to print a patient report that includes patient data for pre-op and the procedure itself. The combination of printing a patient report and the automatic data logging features decrease the amount of time and effort a nurse or technician must spend regarding patient condition during the course of a procedure. Printer 70 receives data signals from a printer interface (e.g., Parallel Systems CK205HS), which is located on the main logic board. Printer 70 may be a thermal printer (e.g., Advanced Printing Systems (APS) ELM 205HS).

Memory card reader 85, which includes a slot in the outer casing of procedure unit 12, allows flash memory card 84 to be inserted and removed from procedure unit 12. Flash memory card 84 is a solid-state storage device used for easy and fast information storage of the data log generated by procedure unit 12. Flash memory card 84 is well known in the computer field and one of the many suitable removable flash memory cards as for example, a SmartMedia Card, a Multi-Media Card, or a CompactFlash Card, may be used with memory card reader 85. The data is stored so that it may be retrieved from flash memory card 84 at a later time. In one embodiment, memory card reader 85 accepts flash memory card 84 containing software to upgrade the functionality of patient care system 5. Data port 88 can include, but is not limited to, a standard serial port, a USB port, a RS232 port, or an Ethernet port. Data port 88 is useful to link procedure unit 12 to an external printer to print a patient report or to transfer electronic files to a personal computer or mainframe. In an alternate embodiment, data port 88 can be a wireless transmitter interacting with a wireless receiver connected to a printer or an external computer or mainframe.

Referring also to FIGS. 4-B and 4-C, procedure unit 12 delivers fluid to a patient via an infusion pump, such as a peristaltic infusion pump 72 (e.g., B-Braun McGaw). Peristaltic infusion pump 72 is integrally attached to procedure unit 12. A peristaltic infusion pump uses peristaltic fingers to create a wavelike motion to induce fluid flow inside a flexible tube connected to a fluid reservoir. Drug cassette 64 is a generally rectangular shaped structure that is placed adjacent to peristaltic infusion pump 72. Drug cassette 64 is preferably made of a rigid thermoplastic such as, for example, polycarbonate. Drug cassette 64 has an internal cavity that houses IV tubing 76, preferably made of a flexible thermoplastic such as, for example, polypropylene (e.g., Kelcourt). Drug cassette 64 accurately and reliably positions exposed IV tubing 76 in contact with the peristaltic fingers of peristaltic infusion pump 72. IV tube set 76 attaches to fluid vial 68, and the majority of the length of IV tube set 76 is contained within drug cassette 64. A small portion of IV tube set 76 lies external to drug cassette 64 to facilitate the interaction with peristaltic pump 72. IV tubing 76 is coiled within drug cassette 64 and has a length to reach a patient removed from the procedure unit 12. Mounted upon one inner wall of drug cassette 64 is fluid detection sensor 302. Fluid detection sensor 302 may be any one of known fluid sensors, such as the MTI-2000 Fotonic Sensor, or the Microtrak-II CCD Laser Triangulation Sensor both by MTI Instruments Inc. Fluid detection sensor 302 can be fixedly attached to drug cassette 64 using an attachment means including, but not limited to, glue, mechanical fasteners, screws, and ultrasonic welding. Preferably, IV tube set 76 runs through fluid detection sensor 302 before exiting drug cassette 64.

In one embodiment of a method of operation, procedure unit 12 in combination with drug cassette 64 and peristaltic infusion pump 72 "auto prime" IV tubing 76 so the clinician does not have to take the time to manually prime IV tubing 76. Drug cassette 64 provides interlocks during the "auto prime" process to prevent the clinician from accessing the IV tubing 76 and inadvertently connect IV tubing 76 to the patient. After the auto prime feature is complete, however, the interlock is disabled and the user is able to access the IV tubing 76, through, for example an access door, which during the auto prime feature is locked in a closed position.

Referring also to FIG. 4-A, a nurse or clinician initiates the auto priming system by pressing a button on either bedside touch screen assembly 22 or procedure touch screen assembly 62, step 350. Upon receiving the command to initiate the auto priming system, peristaltic pump 72 activates and begins a new pump cycle, step 352. Peristaltic pump 72 displaces fluid from fluid vial 68 through the length of IV tube set 76, step 354. Fluid detection sensor 302 monitors the extreme end of the IV tube set 76 for the presence of fluids, step 356.

Fluid detection sensor 302 continuously monitors for the presence of fluid within IV tube set 76, step 356. If no fluid is detected, the nurse or technician is notified by either auditory or visual alert indicating that the auto priming process is not complete, step 358. After the alert stating that priming is not complete is given, the main logic board commands peristaltic infusion pump 72 to continue operating, step 352. This process continues through steps 352-356 until fluid detection sensor 302 detects the presence of fluid and the main logic board commands peristaltic infusion pump 72 to stop until further notice, step 360. After the pump cycle ceases, the nurse or technician is notified by either a visual alert on either bedside unit 10 or procedure unit 12, or by an auditory alert indicating the auto priming system has successfully primed the pump, step 362.

FIG. 4-C shows an alternate embodiment of the automatic priming system. Fluid detection sensor 302 is integrated with peristaltic pump 72 or another stable structure adjacent to drug cassette 64. In this embodiment, drug cassette 64 contains two exposed portions of IV tube set 76, a first portion 320, and a second portion 322. First portion 320 allows peristaltic pump 72 to manipulate IV tube set 76 in order to pump fluid through the line. Second portion 322 is placed adjacent to fluid detection sensor 302. Upon detection of fluid in second portion 322, peristaltic pump 72 continues to operate for a short time to ensure that no air remains in IV tube set 76. This time is determined by the main logic board located inside procedure unit 12 calculating the length of IV tube set 76 downstream second portion 322 and the speed at which peristaltic pump 72 is operating. Upon the allotted time has expired, peristaltic pump 72 will cease the pump cycle and IV tube set will be fully primed.

Figure 5:
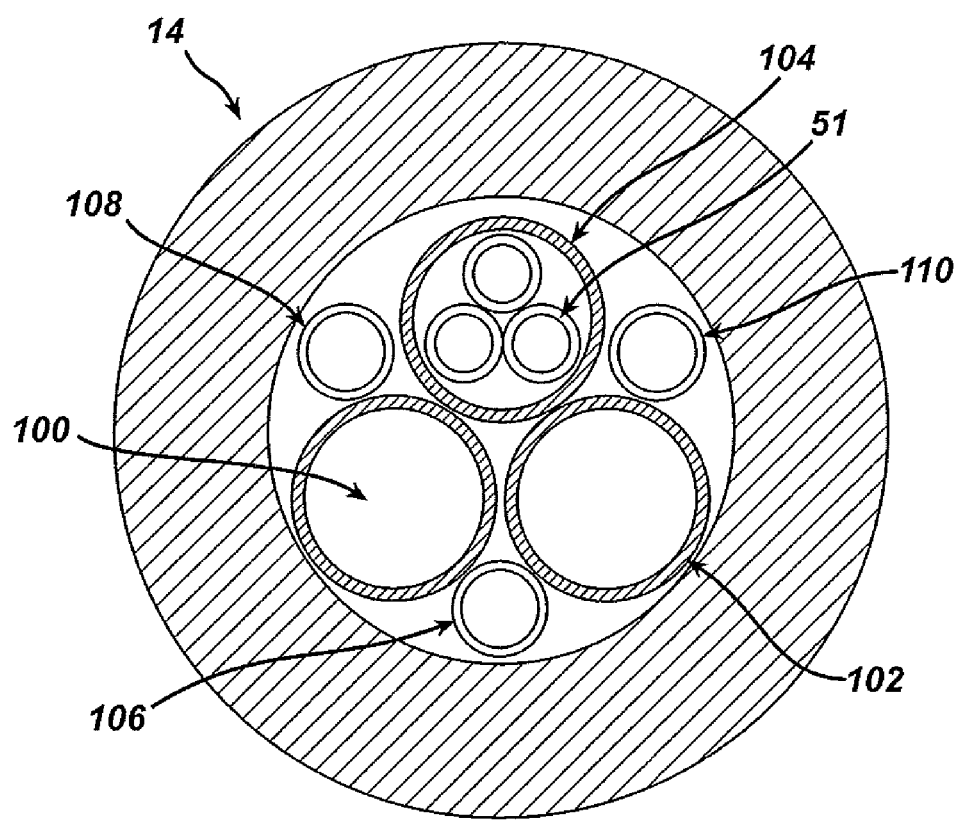
FIG. 5 is a cross-sectional view of the communication cable.

Referring now to FIG. 5, communication cable 14 contains a plurality of centralized pneumatic tubes surrounded by a plurality of electrical wires. Oxygen conduit 100 is a pneumatic tube that delivers oxygen traveling from an external oxygen source through procedure unit 12 to bedside unit 10. Oxygen conduit 100 runs the length of communication cable 14 and terminates at oral nasal cannula 48. Exhaled gas conduit 102 is also a pneumatic tube that transports a patient's exhaled respiratory gases from oral nasal cannula 48 through cable pass-through connection 15 and terminates in procedure unit 12. ECG conduit 104 contains a plurality of electrical wires known as ECG leads 51. ECG leads 51 receive electrical signals from ECG pads 50 that are communicated to procedure unit 12 for data processing. NIBP conductor 106 transmits processed information of a patient's blood pressure from bedside unit 10 to procedure unit 12. Pulse oximeter conductor 108 transmits processed information of a patient's oxygen saturation level from bedside unit 10 to procedure unit 12. ART response conductor 110 transmits processed information regarding a patient's response to ART stimuli from bedside unit 10 to procedure unit 12.

Figure 7:
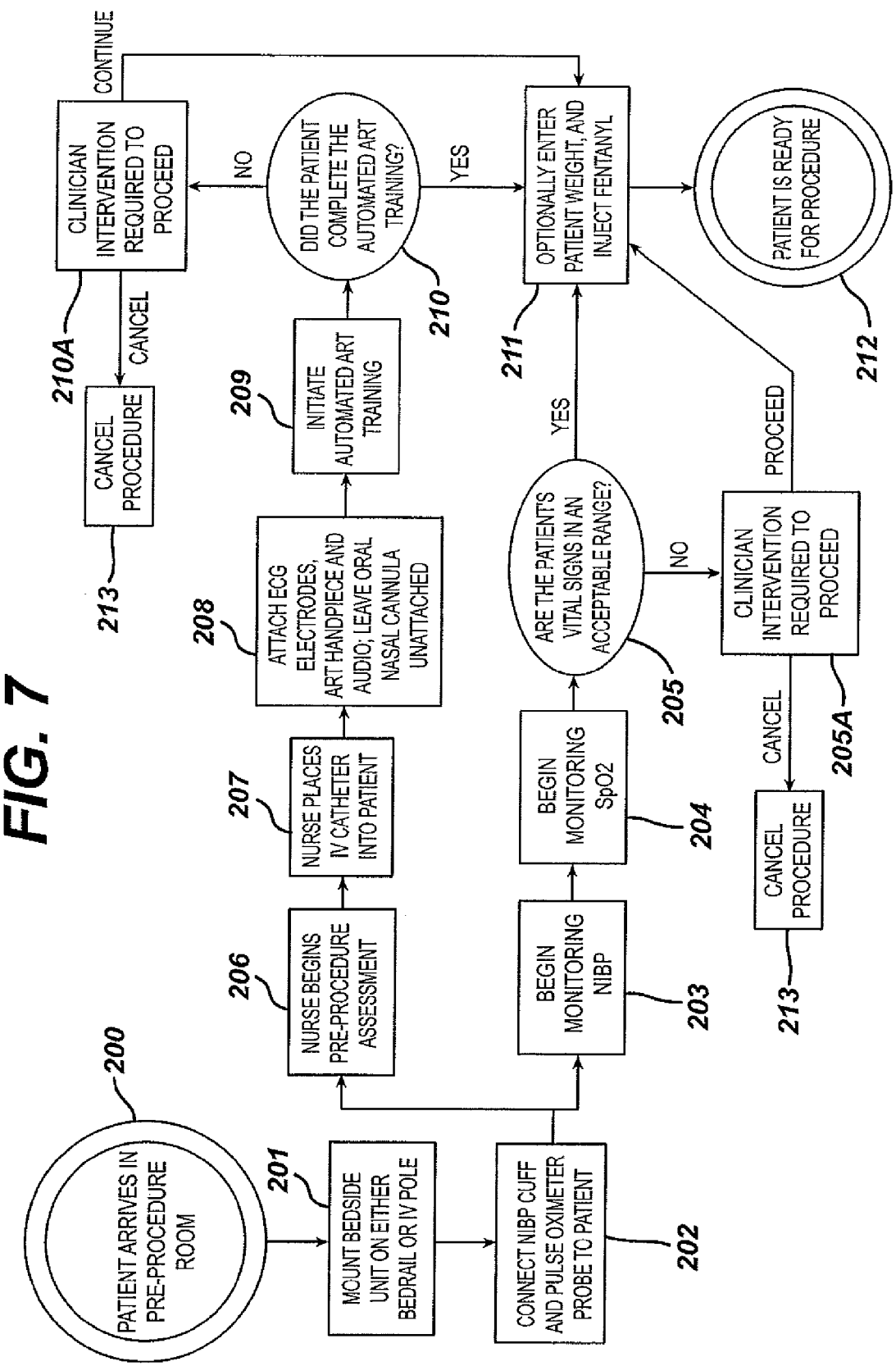
FIG. 7 is an overview data-flow diagram depicting the pre-medical procedure aspect of the invention.

As shown in FIG. 7, a data flow diagram outlines the typical process of the pre-procedure room. As shown, the patient arrives in the pre-procedure room, step 200. A nurse or technician mounts bedside unit 10 to either the bedrail or IV pole, step 201. Bedside unit 10 is equipped with an IV pole clamp or a quick connect to quickly and easily mount the unit on either the bedrail or IV pole. Once bedside unit 10 is in place, the nurse or clinician may connect NIBP cuff 58 and pulse oximeter probe 60 to the patient, step 202. These connections are made between the patient and bedside unit 10. Bedside unit 10 will automatically begin monitoring parameters such as, for example, diastolic and systolic blood pressure, mean arterial pressure, pulse rate, oxygenation plethysmogram, and oximetry value, steps 203,204. The readings taken by bedside unit 10 will be displayed for the nurse or technician on bedside touch screen assembly 22. While patient parameters are being monitored, the nurse or technician is free to perform other tasks. As is customary with current practice, the nurse or technician may need to complete a pre-procedure assessment, step 206. The pre-procedure assessment may include recording patient vital signs, determining any known allergies, and determining patient's previous medical history. Once the nurse or technician has completed the pre-procedure assessment, step 206, the nurse or technician may start the peripheral IV by placing a catheter in the patient's arm, step 207. The IV catheter is connected to the primary IV drip device such as, for example, a 500 mL bag of saline fluid. Upon completion of the above activities, the nurse or technician begins to attach ECG pads 50, ART handpiece 57, ART earpiece 55 and oral nasal cannula 48 to the patient, step 208. Preferably, patient care system 5 has the capability to automatically detect and recognize the proper connection of the monitors when they are connected from the patient to bedside unit 10.

Once the patient is connected to the above-mentioned items, the nurse or technician may explain ART system 52 to the patient. This explanation may involve the nurse or technician instructing the patient to respond to auditory stimulation from ART earpiece 55 and/or tactile stimulation from ART handpiece 57 by squeezing ART handpiece 57. If the patient fails to respond to either auditory or tactile stimulation, the intensity of the stimulation will increase until the patient responds successfully. At this point, the nurse may initiate an automated ART training, step 209. Automated ART training is a program run by bedside unit 10 that teaches the patient how to detect an ART stimulus and how to respond to that stimulus and sets a baseline patient response to the stimulus as disclosed in the previously referenced U.S. patent application Ser. No. 10/674,160. The nurse or technician is free to perform other patient related tasks while the patient is participating in the automated ART training Bedside unit 10 will display the automated ART training status so the nurse or technician can quickly determine if the patient is participating in the automated training. The patient must successfully complete the automated ART training to proceed, step 210; if the patient fails to complete the training a nurse or other clinician must intervene and determine if the patient may continue, step 210-A. If the clinician decides the user may proceed, then the patient will proceed to step 211; if the clinician decides the patient is unable to continue, then the procedure will be canceled, step 213. The user may customize the automated ART training to automatically repeat at specified intervals (i.e. 10 minutes) if the patient is required to wait to enter the procedure room. This will help to instill the newly learned response.

In addition to successfully completing automated ART training, the patients parameters must be in an acceptable range, step 205. The clinician may decide upon what an acceptable range is by inputting this information into bedside unit 10 by means of bedside touch screen assembly 22. If any one of the parameters being monitored falls outside a given range, the patient will not be permitted to undergo a procedure until a nurse or other clinician examines the patient to determine whether or not the patient may continue, step 205-A. If the clinician decides the patient is able to continue, the patient will proceed to step 211, if the clinician decides the patient is unable to continue, then the procedure will be cancelled, step 213. Just prior to leaving the pre-procedure room for the procedure room, the nurse administers a predetermined low dose of an analgesic drug, step 211 such as, for example, a 1.5 mcg/kg of Fentanyl. After the injection of the analgesic drug, the patient is ready to be moved to the procedure room, step 212.

Figure 8:
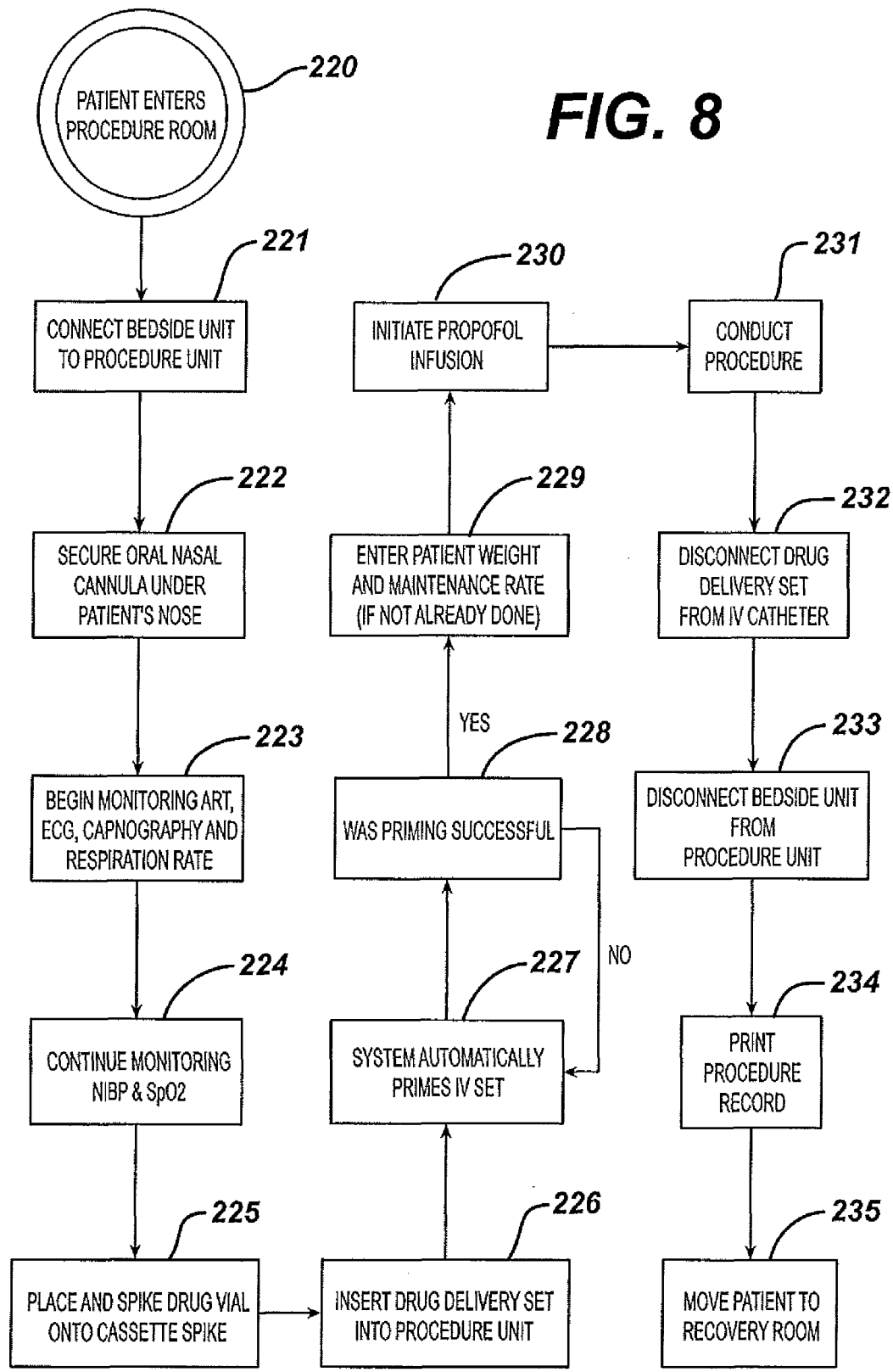
FIG. 8 is an overview data-flow diagram depicting the medical procedure aspect of the invention.

FIG. 8 is a flow chart illustrating the implementation of the invention while the patient is in the procedure room. As shown, the patient and bedside unit 10 are moved into the procedure room, step 220 and is received by the physician and procedure nurse. Bedside unit 10 may be connected to procedure unit 12 upon the patient entering the procedure room, step 221. Upon connection, the NIBP, pulse and oximetery history from the patient will automatically up-load to procedure unit 12 displaying patient history for the last period of monitoring. In addition to NIBP and pulse oximeter history, a record verifying the patient has completed ART training will also be uploaded. Upon connection of bedside unit 10 to procedure unit 12, the small display on bedside unit 10 changes immediately from a monitoring screen to a remote entry screen for procedure unit 12. Display information form bedside unit 10 is automatically transferred to procedure unit 12.

At this point, the procedure nurse may secure oral nasal cannula 48 to the patient's face, step 222. Procedure unit 12 may begin monitoring patient parameters such as, for example, ART, ECG, and capnography now that all connections between the patient and procedure unit 12 are complete, step 223. Procedure unit 12 will continue monitoring patient parameters such as, for example, NIBP, pulse, and oximetery, step 224. Next the procedure nurse may place and spike a standard drug vial, step 225 onto drug cassette 64. Drug cassette 64 has an integrated drug vial spike that serves to puncture the rubber vial stopper as well as to allow fluid from the drug vial to enter drug cassette 64. Next the procedure nurse needs to place drug cassette 64 adjacent to peristaltic infusion pump 72 making sure that the exposed portion of IV tubing 76 lines up with the peristaltic fingers, step 226. Once the fluid vial and drug cassette 64 are loaded correctly, the nurse may autoprime IV tubing 76. In one embodiment, the procedure nurse would press a button located upon procedure unit 12 to initiate the autopriming, step 227. Autopriming is the automatic purging of air from IV tubing 76. procedure unit 12 continuously monitors the autopriming process to determine the overall success of the autopriming. If procedure unit 12 fails to properly purge IV tubing 76, a warning notification is made to the user so that the procedure nurse may repeat the autopriming sequence until IV tubing 76 is successfully purged, step 227.

Upon successful completion of the autopriming sequence, the procedure nurse may enter the patient weight in pounds while the physician may enter the initial drug maintenance dose rate as well as dose method; normal or rapid infusion, step 229. After the patient weight and dose rate have been inputted, the physician or procedure nurse may initiate drug infusion, step 230. While the drug is taking effect upon the patient, the physician may perform standard procedure related activities such as, for example, test the scope, and apply any topical anesthetic. Once the drug has taken the desired effect upon the patient, the physician and procedure nurse are free to conduct the procedure, step 231. Upon completion of the procedure, the clinician may disconnect the drug delivery cassette from the catheter, step 232 and disconnect the bedside unit from the procedure unit, step 233. If the clinician so desires, procedure unit 12 may print a record of the patient's physiological parameters from printer 70 at this time, step 234. Included on the print out of the procedure record are patient monitoring data such as, for example, NIPB, pulse oximetery, capnography, respiration rate, and heart rate. Other system events included in the print out are, ART competency, ART responsiveness during the procedure, oxygen delivery history, drug dose, monitoring intervals, drug bolus amount and time, and total drug volume delivered during the procedure. The printout includes a section where the procedure nurse may enter in notes of her own, such as, for example, additional narcotic delivered, topical spray used, Ramsey Sedation Scale, procedure start and finish time, cautery unit and settings used, cautery grounding site, dilation equipment type and size, and Aldrete Score. After printing the patient record, the patient may then be moved to the recovery room, step 235.

Figure 9:
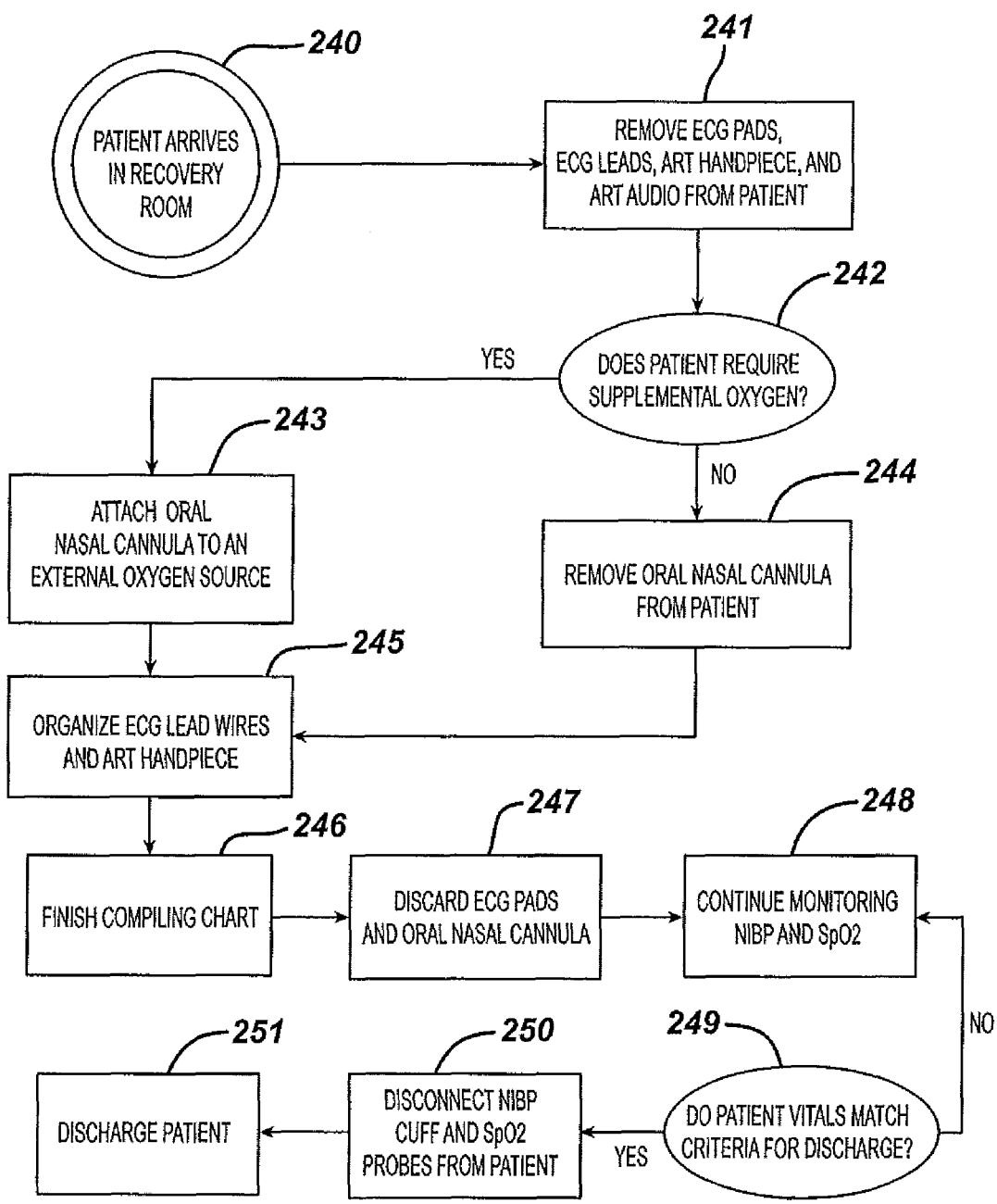
FIG. 9 is an overview data-flow diagram depicting the post-medical procedure aspect of the invention.

As shown in FIG. 9, a flow chart illustrating the implementation of the invention while the patient is in the recovery room. As shown, the patient arrives in the recovery room 240 still attached to bedside unit 10 after leaving the procedure room. At this point, bedside unit 10 may be operating on either battery or AC power. Upon entering the room, the attending clinician may remove the ECG pads, ECG lead wires, ART handpiece, and ART earpiece from the patient 241. Depending upon clinician preference and status of the patient, the patient may require supplemental oxygen while in the recovery room 242. If the patient does require supplemental oxygen, oral nasal cannula 48 is left on the patients face and oxygen is accessed from an external source such as, for example, a headwall or tank. The nurse or technician would disconnect oral nasal Cannula 48 from bedside unit 10, plug it directly into a standard oxygen delivery extension set, and set the desired oxygen flow rate, step 243. If no supplemental oxygen is required in the recovery room, the nurse or technician may remove oral nasal cannula 48 from the patient 244.

The nurse or technician may now organize ECG leads 51 and ART handpiece 57 and place near bedside unit 10 to be used on the next patient 245. The nurse or technician may need to fill out additional information on the patient record 246. The nurse or technician will most likely write notes describing the patient's condition during recovery and record NIBP, pulse rate and oximetery values of the patient during recovery. ECG pads 50 and oral nasal cannula 48 may be discarded at this point into a standard waste container located in the recovery room 247. It is important to note that bedside unit 10 is still collecting data related to NIBP, pulse rate, and pulse oximetery 248. The nurse or technician must determine if the patient is ready to be discharged 249. Criteria for discharge vary among patient care facilities; however an Alderate score of 10 is common for discharge. Other measures of discharge criteria include skin color, pain assessment, IV site intact, NIBP, pulse, respiration rate, and oximetery values all must be close to the measurement taken in pre-procedure. If the patient does not meet any of these criteria, it is recommended that the patient receive additional monitoring 248. Once a patient is cleared for discharge, the nurse or technician disconnects NIBP cuff 58, pulse oximeter Probe 60, and if not done so already, oral nasal cannula 48 from the patient 250. Once all the above is completed, the patient may be discharged from the care facility 251.

The foregoing description of several expressions of embodiments and methods of the invention has been presented for purposes of illustration. It is not intended to be exhaustive or to limit the invention to the precise forms and procedures disclosed, and obviously many modifications and variations are possible in light of the above teaching. It is intended that the scope of the invention be defined by the claims appended hereto.

We claim:

1. A method for monitoring a patient and delivering at least one drug during a medical procedure in a medical care facility comprising the steps of:
   a) locating the patient in a first location of the medical care facility and connecting to the patient at least one sensor for monitoring at least one physiological parameter of the patient;
   b) obtaining a first housing having a first microprocessor-based patient unit having at least one first connection point for receiving input signals from the at least one sensor and at least one second connection point for outputting patient physiological parameters;
   c) locating the patient in a second location of the medical care facility, connecting the at least one second connection point to a second housing having a second microprocessor-based procedure unit, and delivering the drug to the patient and performing a medical procedure on the patient, wherein at least a portion of the medical procedure is controlled by the second microprocessor-based procedure unit and;
   d) delivering oxygen to the patient by way of the second connection point.

2. The method of claim 1 further comprising the steps of inputting to the first microprocessor-based patient unit physical attributes of the patient.

3. The method of claim 1 further comprising the step of querying the patient to determine a level of consciousness of the patient.

4. The method of claim 3 further comprising the step of the patient activating a response device.

5. The method of claim 1 further comprising the step of delivering the drug via an IV tube and priming the IV tube before delivering the drug to the patient.

6. The method of claim 5, wherein priming the IV tube is automatically performed by the procedure unit.

7. A method for monitoring a patient and delivering at least one drug during a medical procedure in a medical care facility comprising the steps of:
   a) locating the patient in a first location of the medical care facility and connecting to the patient at least one sensor for monitoring at least one physiological parameter of the patient;
   b) obtaining a first housing having a first microprocessor-based patient unit having at least one first connection point for receiving input signals from the at least one sensor and at least one second connection point for outputting patient physiological parameters;
   c) locating the patient in a second location of the medical care facility, connecting the at least one second connection point to a second housing having a second microprocessor-based procedure unit, and performing a medical procedure on the patient, wherein at least a portion of the medical procedure is controlled by the second microprocessor-based procedure unit and;
   d) inputting exhaled respiratory gases from the patient to the procedure unit by way of the second connection point.

8. The method of claim 7 further comprising the step of delivering oxygen to the patient by way of the second connection point.

* * * * *